(12) United States Patent
Ota et al.

(10) Patent No.: US 11,730,348 B2
(45) Date of Patent: Aug. 22, 2023

(54) ENDOSCOPE

(71) Applicant: OLYMPUS CORPORATION, Tokyo (JP)

(72) Inventors: Tsukasa Ota, Hachioji (JP); Yuka Ide, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 460 days.

(21) Appl. No.: 16/289,751

(22) Filed: Mar. 1, 2019

(65) Prior Publication Data

US 2019/0191965 A1 Jun. 27, 2019

Related U.S. Application Data

(63) Continuation of application No. PCT/JP2017/015437, filed on Apr. 17, 2017.

(30) Foreign Application Priority Data

Sep. 6, 2016 (JP) .................................. 2016-173836

(51) Int. Cl.
*A61B 1/005* (2006.01)
*A61B 1/00* (2006.01)
(Continued)

(52) U.S. Cl.
CPC .......... *A61B 1/0051* (2013.01); *A61B 1/0057* (2013.01); *A61B 1/00147* (2013.01);
(Continued)

(58) Field of Classification Search
CPC ........ A61B 1/005–0051; A61B 1/0055; A61B 1/0057; A61B 1/0052; A61B 1/0053;
(Continued)

(56) References Cited

U.S. PATENT DOCUMENTS 3,583,393 A * 6/1971 Takahashi ............ A61B 1/0055
138/120
4,686,963 A * 8/1987 Cohen .................. A61B 1/0055
138/120
(Continued)

FOREIGN PATENT DOCUMENTS

EP 1927312 A1 6/2008
JP 62186836 A * 9/1987 ........... A61B 1/0057
(Continued)

OTHER PUBLICATIONS

International Search Report dated Jun. 27, 2017 issued in PCT/JP2017/015437.

*Primary Examiner* — Ryan N Henderson
(74) *Attorney, Agent, or Firm* — Scully, Scott, Murphy & Presser, P.C.

(57) ABSTRACT

An endoscope is provided with: a wire; a distal end nodal ring, in which the wire is arranged immediately below a first through hole including openings at predetermined positions on the inner circumferential face and an outer circumferential face of the distal end nodal ring; a distal end member including a small diameter portion arranged to be fitted in a distal end side inner circumferential face of the distal end nodal ring and a large diameter portion provided on a distal end side of the small diameter portion, the large diameter portion having a diameter larger than a diameter of the small diameter portion; an accommodating portion formed on an outer circumferential face side of the small diameter portion, the first end portion of the wire being accommodated in the accommodating portion; and a relief portion formed by the accommodating portion extending to the large diameter portion.

7 Claims, 7 Drawing Sheets

(51) Int. Cl.
*A61B 1/05* (2006.01)
*G02B 23/24* (2006.01)
*A61B 1/01* (2006.01)
*A61B 1/06* (2006.01)

(52) U.S. Cl.
CPC ............... *A61B 1/05* (2013.01); *G02B 23/24* (2013.01); *A61B 1/005* (2013.01); *A61B 1/01* (2013.01); *A61B 1/0676* (2013.01); *G02B 23/2476* (2013.01)

(58) Field of Classification Search
CPC ... A61B 1/0056; A61B 1/0058; A61B 1/0008; A61B 2017/003; A61B 2017/00318; A61B 2017/00323; A61B 2017/00314; A61B 2017/00327; A61M 25/0133; A61M 25/0147; A61M 2025/015

See application file for complete search history.

(56) References Cited

U.S. PATENT DOCUMENTS

| | | | | |
|---|---|---|---|---|
| 4,726,355 | A | * | 2/1988 | Okada ................... F16G 13/16 356/241.6 |
| 5,348,975 | A | * | 9/1994 | Chandraratna ...... C07D 311/58 549/370 |
| 5,438,975 | A | * | 8/1995 | Miyagi ................. A61B 1/0055 600/141 |
| 2006/0074383 | A1 | * | 4/2006 | Boulais ................ A61B 1/0016 604/95.04 |
| 2008/0287736 | A1 | * | 11/2008 | Yamazaki ............ A61B 1/0057 600/118 |
| 2009/0137875 | A1 | | 5/2009 | Kitagawa et al. |
| 2009/0227842 | A1 | * | 9/2009 | Ando .................. A61B 1/0055 600/146 |

FOREIGN PATENT DOCUMENTS

| | | |
|---|---|---|
| JP | 2001-149307 A | 6/2001 |
| JP | 2002-236260 A | 8/2002 |
| JP | 2007-082815 A | 4/2007 |
| JP | 2010-029488 A | 2/2010 |
| JP | 2013-141497 A | 7/2013 |
| WO | WO 2007/034664 A1 | 3/2007 |

\* cited by examiner

ENDOSCOPE

CROSS REFERENCE TO RELATED APPLICATION

This application is a continuation application of PCT/JP2017/015437 filed on Apr. 17, 2017 and claims benefit of Japanese Application No. 2016-173836 filed in Japan on Sep. 6, 2016, the entire contents of which are incorporated herein by this reference.

BACKGROUND OF THE INVENTION

1. Field of the Invention

The present invention relates to an endoscope provided with a pulling wire to cause a bending portion to bend.

2. Description of the Related Art

An endoscope has an elongated insertion portion and is provided with an observation optical system and the like for picking up an observation image of an observed region on a distal end side of the insertion portion. Among endoscopes, some endoscopes are provided with a bending portion on a distal end portion side of the insertion portion. In an endoscope provided with the bending portion on the insertion portion, insertion into a depth can be easily performed, and it becomes possible to direct the observation optical system located on the distal end side in a desired direction.

The bending portion is configured mainly with a bending tube and bending rubber covering the bending tube. The bending tube is, for example, a bending piece set configured with a plurality of bending pieces that are turnably and continuously provided or a rigid pipe for bending portion that is bendably configured by providing a plurality of slots on a rigid pipe. The bending tube is configured to bend in two directions of upward and downward directions or four directions of upward, downward, left and right directions.

In the bending tube, a plurality of pulling wires corresponding to the bending directions are inserted. Distal ends of the pulling wires are fixed to a distal end nodal ring or the like constituting a most distal end of the bending tube. Proximal ends of the pulling wires are fixed to a bending operation apparatus arranged in an operation portion provided on a proximal end side of the insertion portion. According to the configuration, the bending portion bends by a user operating the bending operation apparatus to pull or loosen the pulling wires.

FIG. 7 of Japanese Patent Application Laid-Open Publication No. 2001-149307 discloses that distal ends of pulling wires are fixed to a connection member. FIG. 9 discloses a technique for directly laser-welding the connection member to an inner circumferential face of a nodal ring to join the connection member.

FIG. 18(a) of Japanese Patent Application Laid-Open Publication No. 2002-236260 shows a wire fixing portion provided by cutting and bending a side wall of a distal end piece. Distal ends of pulling wires are fixed to the wire fixing portion by solder or the like. FIG. 18(b) of Japanese Patent Application Laid-Open Publication No. 2002-236260 shows a notch portion for confirming the wire fixing portion.

SUMMARY OF THE INVENTION

An endoscope of an aspect of the present invention is provided with: a wire including a first end portion and a second end portion, the wire being inserted in an endoscope insertion portion; a tubular member, the first end portion side of the wire being arranged along an inner circumferential face of the tubular member, the first end portion side of the wire being joined at a predetermined position on a distal end of the tubular member by welding, the wire being arranged immediately below a first through hole including openings at predetermined positions on the inner circumferential face and an outer circumferential face of the tubular member; a distal end member including a small diameter portion arranged to be fitted in a distal end side inner circumferential face of the tubular member and a large diameter portion provided on a distal end side of the small diameter portion, the large diameter portion having a diameter larger than a diameter of the small diameter portion; an accommodating portion formed on an outer circumferential face side of the small diameter portion, the first end portion of the wire being accommodated in the accommodating portion; and a relief portion formed by the accommodating portion extending to the large diameter portion.

DETAILED DESCRIPTION OF THE PREFERRED EMBODIMENT(S)

Figure 1:
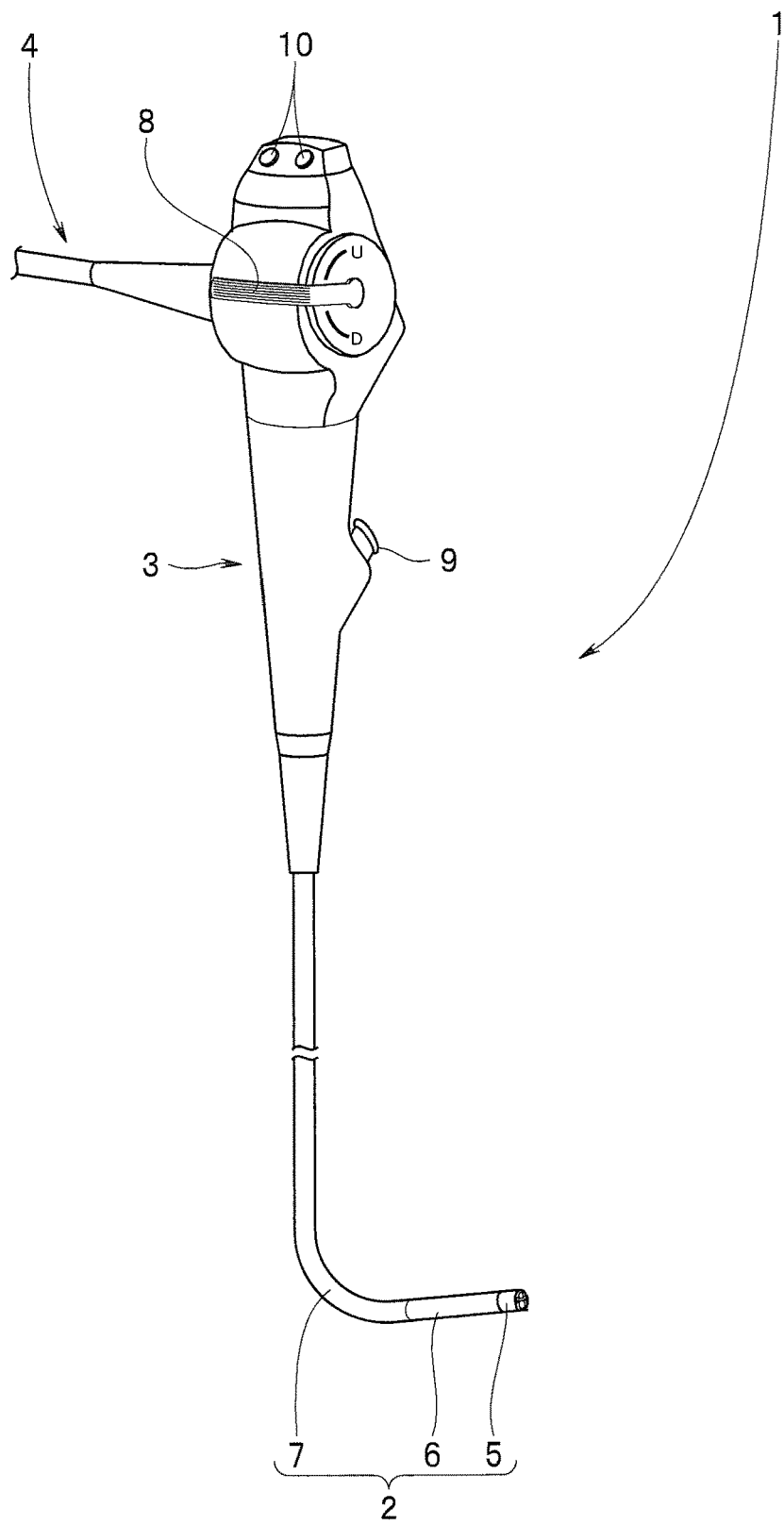
FIG. 1 is a diagram illustrating an endoscope having a bending portion as a part of an insertion portion.

An embodiment of the present invention will be described below with reference to drawings.

Note that, on each drawing used in the description below, a reduced scale may be different for each component so that the component is in a size recognizable on the drawing. That is, the present invention is not limited only to the number of components, shapes of the components, a size ratio among the components, and a relative positional relationship among the respective components illustrated on the drawings.

An endoscope 1 shown in FIG. 1 is mainly provided with an endoscope insertion portion (hereinafter abbreviated as an insertion portion) 2, an endoscope operation portion (hereinafter abbreviated as an operation portion) 3 and a universal cord 4. The insertion portion 2 has a small diameter and is configured with a distal end portion 5, a bending portion 6 and a flexible tube portion 7 continuously provided in that order from a distal end side.

Figure 2:
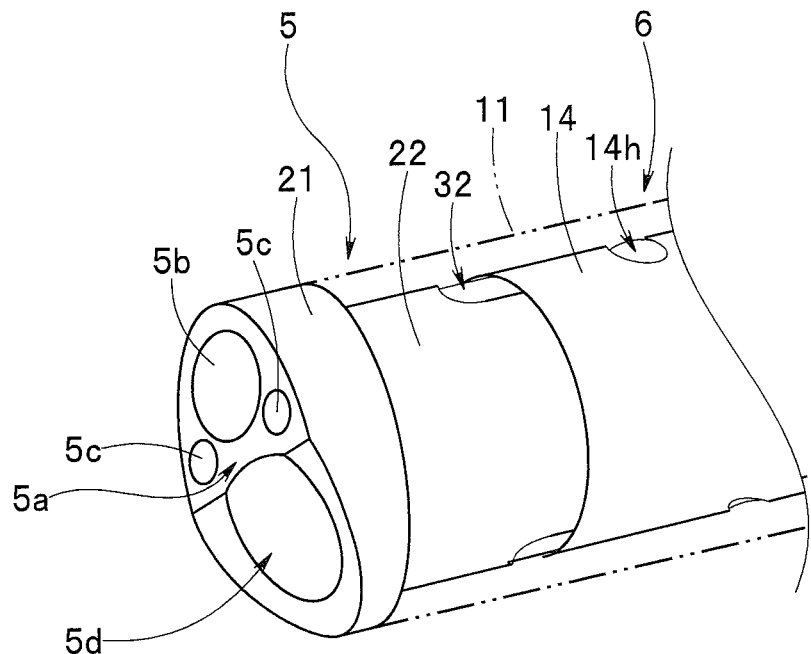
FIG. 2 is a diagram illustrating a configuration of a distal end face, and a relationship between a distal end rigid member and a distal end nodal ring.
Figure 3:
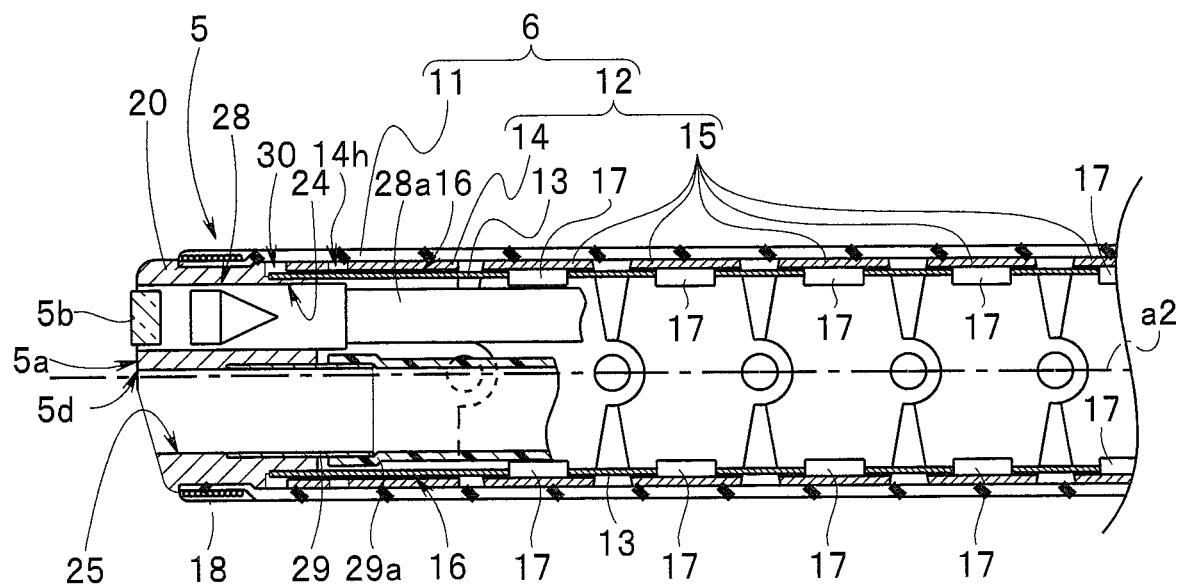
FIG. 3 is a longitudinal cross-sectional view illustrating a configuration of a distal end side of the insertion portion.

On a distal end face 5a of the distal end portion 5, for example, an observation window 5b, two illumination windows 5c, a treatment instrument opening 5d and the like are provided as shown in FIGS. 2 and 3.

The bending portion 6 is provided in the middle of the insertion portion 2 and is configured to bend, for example, in upward and downward directions. As shown in FIG. 3, the bending portion 6 is configured, mainly including bending rubber 11 and a bending tube 12. Pulling wires 13 are inserted in the bending tube 12.

The flexible tube portion 7 is a tube body having flexibility and is configured to passively bend.

As shown in FIG. 1, the operation portion 3 is provided on a proximal end side of the flexible tube portion 7. The operation portion 3 is provided with a bending operation apparatus 8, a treatment instrument insertion slot 9, a plurality of remote switches 10, a suction slot (not shown) and the like. The plurality of remote switches 10 are switches for stopping an endoscopic image displayed on a screen of a display apparatus (not shown) or performing recording, enlargement of an image, switching of illumination light and the like.

The bending operation apparatus 8 is, for example, an L-shaped lever and is turnably shaft-fixed relative to the operation portion 3. The bending operation apparatus 8 is operated when the user causes the bending portion 6 to bend. The pulling wires 13 are pulled or loosened, accompanying an operation of the bending operation apparatus 8, and the bending portion 6 bends in the upward or downward direction.

Note that the bending portion 6 described above is configured to bend in the upward and downward directions. The bending portion 6 may be, however, configured to bend in four directions of upward, downward, left and right directions. In that case, the operation portion 3 is provided with a lever for the left and right directions in addition to the lever for the upward and downward directions. By a turning operation of the operation lever for the left and right directions being performed, a pulling wire for the left or right direction is pulled or loosened, and the bending portion 6 bends in the left direction or the right direction. The bending operation apparatus 8 is not limited to the L-shaped lever but may be a circular-shaped turning knob, a joystick-type stick-shaped lever which is tilt-operated, or the like.

The universal cord 4 extends from a side portion of the operation portion 3. A proximal end portion of the universal cord 4 is provided with an endoscope connector (not shown). The endoscope connector is connected to a light source apparatus which is an external apparatus.

As shown in FIGS. 2 to 4C, the distal end portion 5 is provided with a distal end rigid member 20 which is a frame member. The distal end rigid member 20 is a rigid member made of metal or resin. The distal end rigid member 20 is provided with an image pickup apparatus hole 24, a treatment instrument/suction hole 25, a first illumination hole 26, a second illumination hole 27 and the like which are through holes in an axial direction. Note that it becomes easy to use a high-frequency treatment instrument by causing the distal end rigid member 20 to be made of resin.

As shown in FIG. 3, an image pickup apparatus 28 is arranged in the image pickup apparatus hole 24. Reference numeral 28a indicates a signal cable, which extends from the image pickup apparatus 28. A connection pipe 29 is arranged in the treatment instrument/suction hole 25. Reference numeral 29a indicates a treatment instrument channel tube, and a tube distal end side of the treatment instrument channel tube 29a is fixed to a pipe proximal end side of the connection pipe 29. Illumination fibers (not shown) with distal end faces arranged facing the illumination windows 5c are arranged in the first illumination hole 26 and the second illumination hole 27, respectively.

The bending portion 6 is configured mainly including the bending rubber 11 and the bending tube 12. In the present embodiment, the bending tube 12 is a bending piece set configured with a plurality of bending pieces that are turnably coupled. Therefore, the bending tube 12, which is a bending piece set, is configured by turnably coupling a distal end tubular member (hereinafter referred to as a distal end nodal ring) 14, a plurality of intermediate tubular members (hereinafter referred to as intermediate nodal rings) 15 and a proximal end tubular member (not shown), which are tubular members, from a distal end side in that order. The distal end nodal ring 14 is fixed to a proximal end side of the distal end rigid member 20.

In the bending tube 12, the pulling wires 13 are inserted along a longitudinal axis a2 of the insertion portion 2. Each pulling wire 13 is provided with one end and the other end, and the one end side is joined to a predetermined position on the distal end nodal ring 14 by welding. Reference numeral 16 indicates a joining portion.

The other end of the pulling wire 13 passes through the insertion portion 2 and is extended into the operation portion 3. The other end is fixed to a pulley (not shown) constituting the bending operation apparatus 8 arranged in the operation portion 3.

Note that reference numeral 17 indicates wire guides provided on the intermediate nodal rings 15, and each pulling wire 13 is inserted through the wire guides 17. The bending tube 12 is not limited to a bending piece set but may be a rigid pipe for bending portion that is bendably configured by providing a plurality of slots on a rigid pipe as described before. The longitudinal axis a2 includes the longitudinal axis of the insertion portion 2, a central axis of the distal end rigid member 20 and a central axis of each nodal ring.

The distal end rigid member 20 and the distal end nodal ring 14 will be described with reference to FIGS. 4A to 5.

Figure 4A:
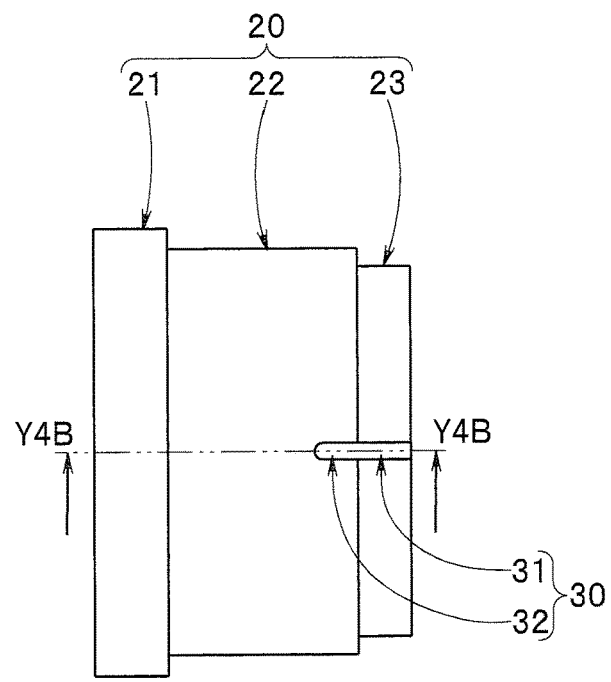
FIG. 4A is a plan view of the distal end rigid member seen from upward.
Figure 4B:
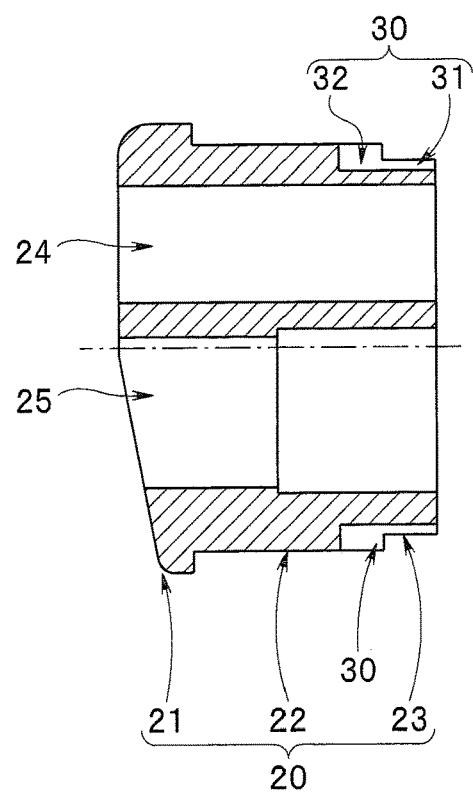
FIG. 4B is a cross-sectional view along a line shown by arrows Y4B in FIG. 4A.
Figure 4C:
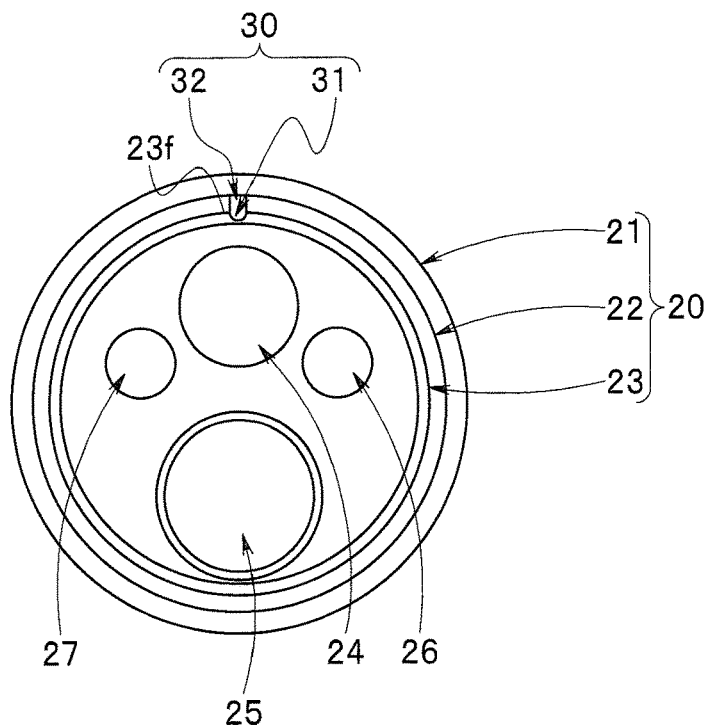
FIG. 4C is a rear view of the distal end rigid member seen from a proximal end face side.
Figure 5:
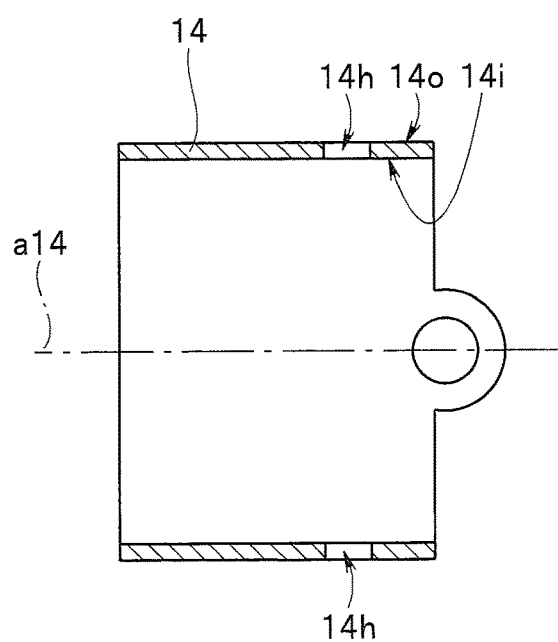
FIG. 5 is a cross-sectional view illustrating the distal end nodal ring.

The distal end rigid member 20 shown in FIGS. 4A, 4B and 4C is in a stepped shape and is provided with, for example, a large diameter portion 21, an intermediate portion 22 and a small diameter portion 23 from the distal end face 5a side in that order. The large diameter portion 21 is an exterior portion and constitutes a distal end outer surface exposed outside the distal end portion 5.

The intermediate portion 22 is a bending rubber covered portion, which is covered with a distal end portion of the bending rubber 11. A bobbin adhesive portion 18 is provided on a distal end side outer circumferential face of the bending rubber 11. The bobbin adhesive portion 18 firmly and closely fixes the distal end portion of the bending rubber 11 to an outer circumferential face of the intermediate portion 22.

The small diameter portion 23 is a distal end nodal ring fixing portion and is arranged being fitted to a distal end side of the distal end nodal ring 14. In an arranged state, an inner circumferential face 14i of the distal end nodal ring 14 and an outer circumferential surface 23f, which is an outer circumferential face of the small diameter portion 23, are integrally fixed by adhesion, joining or the like.

In the present embodiment, the large diameter portion 21 has a diameter larger than a diameter of the intermediate portion 22 by a predetermined dimension, and the intermediate portion 22 has a diameter larger than a diameter of the small diameter portion 23 by a predetermined dimension.

As shown in FIGS. 4B and 4C, on a proximal end face side of the distal end rigid member 20 of the present embodiment, two accommodating grooves 30, which are groove portions, are provided in an opposing positional relationship. The accommodating grooves 30 of the present embodiment correspond to upward and downward directions of the bending portion 6 and are provided at predetermined positions.

One end side portions of the pulling wires 13 are accommodated in the accommodating grooves 30, respectively. As shown in FIG. 4A, each accommodating groove 30 is a stop groove set to a predetermined length and extending along the central axis of the distal end rigid member 20 from the proximal end face of the distal end rigid member 20. In the present embodiment, a terminal end portion of each accommodating groove 30 is located in the middle of the intermediate portion 22. Therefore, each accommodating groove 30 of the present embodiment is provided with a wire accommodating portion 31 provided on the small diameter portion 23 and a relief portion 32 provided on the intermediate portion 22.

A width of the wire accommodating portion 31 is set larger than a dimension of an outer diameter of the pulling wires 13 by a predetermined dimension. In comparison, a depth of the wire accommodating portion 31, that is, a distance from the outer circumferential surface 23f of the small diameter portion 23 to a groove bottom face is set to a same dimension as the outer diameter of the pulling wires 13 or smaller than the outer diameter by a predetermined dimension. On the other hand, a width of the relief portion 32 is a same dimension as the width of the wire accommodating portion 31 or larger than the width of the wire accommodating portion 31. A depth of the relief portion 32 is set to a same dimension as the depth of the wire accommodating portion 31 or set larger than the depth of the wire accommodating portion 31. Note that the depth and width of the wire accommodating portion 31 are set according to the outer diameter of the pulling wires 13.

A configuration of the distal end nodal ring 14 will be described with reference to FIG. 5.

The distal end side of the distal end nodal ring 14 is arranged being fitted to the small diameter portion 23. That is, the inner circumferential face 14i of the distal end nodal ring 14 is arranged on the outer circumferential surface 23f of the small diameter portion 23.

At predetermined positions of the distal end nodal ring 14 of the present embodiment, first through holes 14h, each of which has openings on the inner circumferential face 14i and an outer circumferential face 14o, respectively, are formed. Each first through hole 14h is used as both of a window for visually confirming whether a pulling wire 13 is arranged or not and an indicator to specify a range within which laser light is to be radiated at the time of welding the pulling wire 13 to the distal end nodal ring 14. Note that a diameter of the first through holes 14h is appropriately set in consideration of the diameter of the pulling wires 13. Note that, in FIG. 5, central axes of the first through holes 14h are assumed to be axes orthogonal to a central axis a14 of the distal end nodal ring 14.

In the present embodiment, the first through holes 14h are provided in an opposing positional relationship similarly to the accommodating grooves 30 of the distal end rigid member 20 and provided corresponding to the upward direction and downward direction of the bending portion 6. A state in which the accommodating grooves 30 and the first through holes 14h are arranged on straight lines, respectively, along the longitudinal axis a2 of the insertion portion 2 in a state of the distal end nodal ring 14 being arranged in the small diameter portion 23 of the distal end rigid member 20 is an appropriate attachment state.

Here, joining of a pulling wire 13 to the distal end nodal ring 14 by welding will be described with reference to FIGS. 6A to 6F.

Figure 6A:
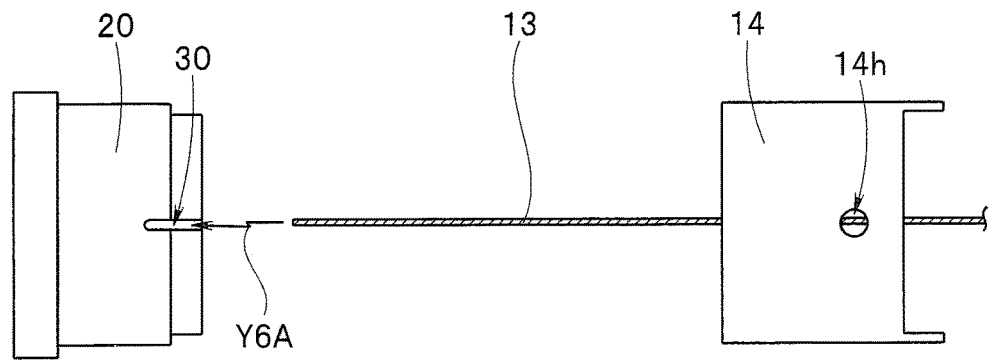
FIG. 6A is a diagram illustrating joining of a pulling wire to the distal end nodal ring and is a diagram illustrating the pulling wire and the distal end nodal ring and the distal end rigid member.

At the time of joining the pulling wire 13 to the distal end nodal ring 14, an operator prepares the distal end rigid member 20 in addition to the pulling wire 13 and the distal end nodal ring 14 shown in FIG. 6A.

First, as shown by an arrow Y6A in FIG. 6A, the operator moves one end side of the pulling wire 13 toward a corresponding accommodating groove 30 of the distal end rigid member 20. Then, while a most distal end portion on the one end side of the pulling wire 13 is accommodated in the relief portion 32, a proximal end side of the most distal end portion of the pulling wire 13 is accommodated in the wire accommodating portion 31.

Figure 6B:
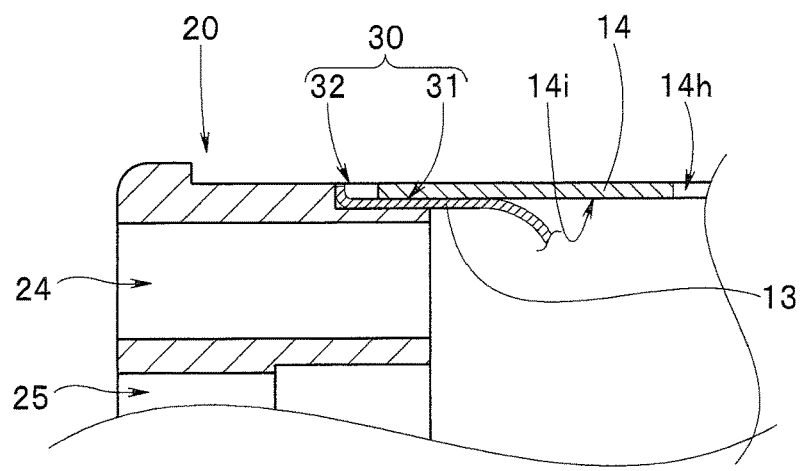
FIG. 6B is a diagram in which the distal end nodal ring is fitted to a small diameter portion and is a diagram illustrating a state in which an inner circumferential face of the distal end nodal ring is in contact with the pulling wire in an accommodating groove 30.

Next, as shown in FIG. 6B, the operator arranges the distal end nodal ring 14 on the small diameter portion 23 of the distal end rigid member 20 in the state of the pulling wire 13 being accommodated in the accommodating groove 30. At this time, a distal end face of the distal end nodal ring 14 is caused to face a proximal end face of the small diameter portion 23 of the distal end rigid member 20 so that the first through hole 14h and the accommodating groove 30 shown in FIG. 6A are arranged on one straight line.

Then, as shown in FIG. 6B, the operator fits the distal end nodal ring 14 to the small diameter portion 23. Then, the inner circumferential face 14i of the distal end nodal ring 14 comes into contact with the pulling wire 13 accommodated in the accommodating groove 30, and the pulling wire 13 is in a stably held state by being sandwiched between an inner face of the wire accommodating portion 31 of the distal end rigid member 20 and the inner circumferential face 14i of the distal end nodal ring 14. Thus, by setting the depth and width of the wire accommodating portion 31 according to the outer diameter of the pulling wires 13, a stably held state can be certainly obtained.

Figure 6C:
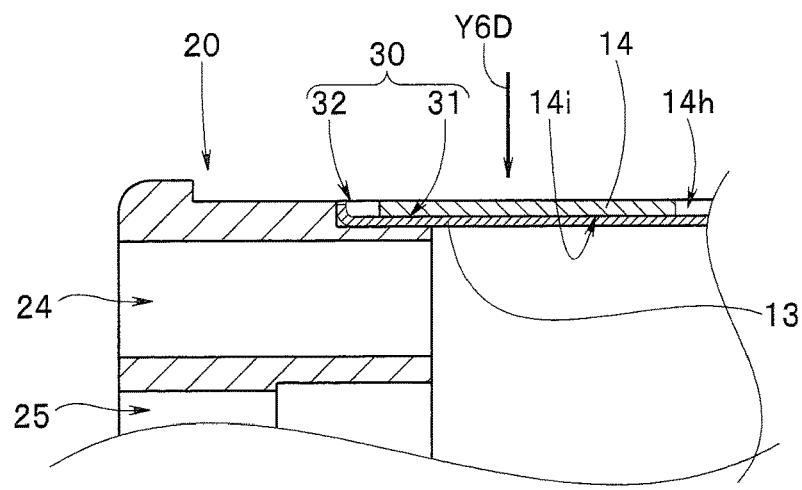
FIG. 6C is a diagram in which the pulling wire is arranged along the inner circumferential face of the distal end nodal ring and is a diagram showing a state in which the pulling wire is located immediately below a first through hole.

Next, as shown in FIG. 6C, the operator causes the pulling wire 13 to be arranged along the inner circumferential face 14i of the distal end nodal ring 14. At this time, the operator performs adjustment so that the pulling wire 13 passes immediately below the first through hole 14h.

Figure 6D:
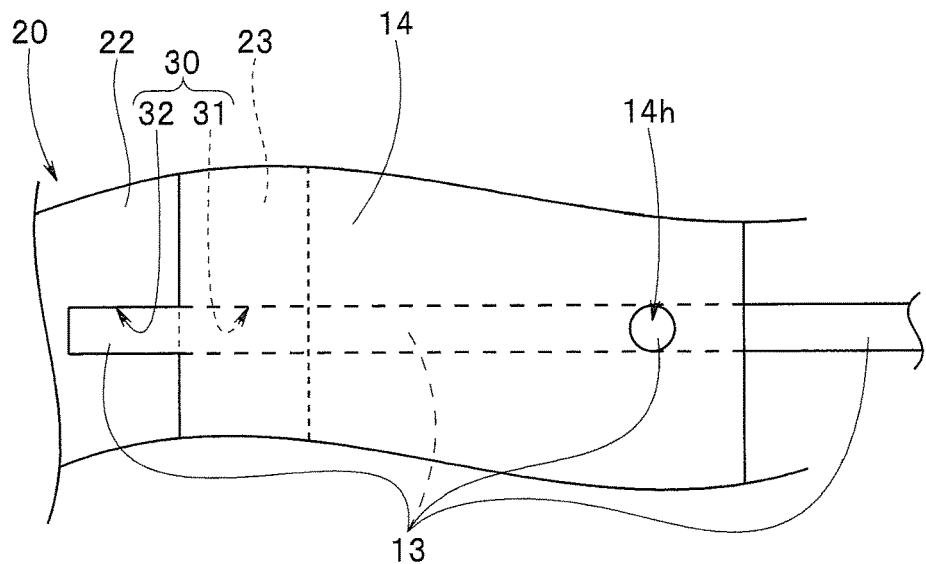
FIG. 6D is a diagram of the distal end rigid member and the distal end nodal ring seen from a direction shown by an arrow Y6D in FIG. 6C.

Then, the operator performs positional adjustment to obtain an appropriate arrangement position and arranges the pulling wire 13 so that the pulling wire 13 can be visually confirmed through the first through hole 14h as shown in FIG. 6D.

Figure 6E:
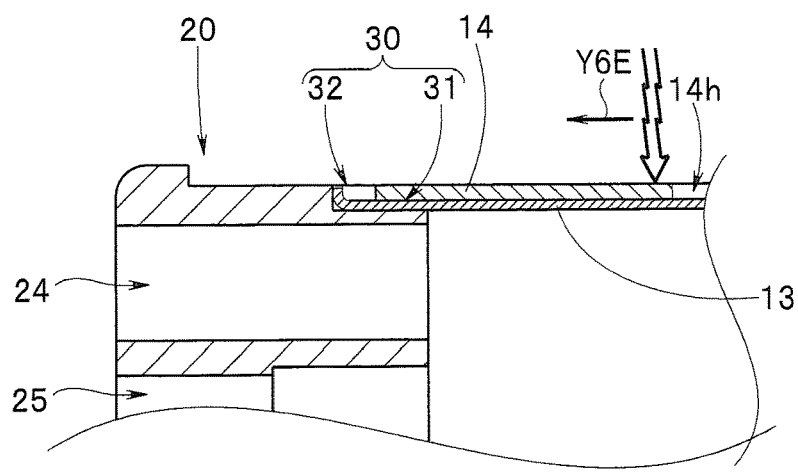
FIG. 6E is a diagram illustrating welding by laser light and is a diagram illustrating a state in which laser light is radiated to a first through hole side surface of the distal end nodal ring.

In the appropriate arrangement state, the operator performs laser welding work. That is, as shown in FIG. 6E, the operator radiates laser light onto a surface of the distal end nodal ring 14 on the first through hole 14*h* side to start welding, and increases a welding range toward the accommodating groove 30 as indicated by an arrow Y6E.

Figure 6F:
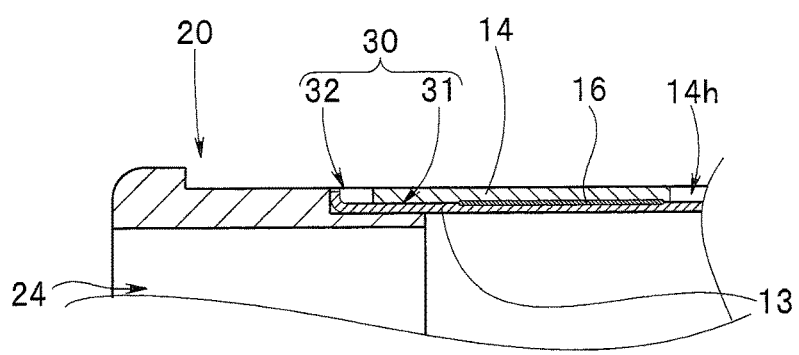
FIG. 6F is a diagram showing a state in which one end side end portion of the pulling wire is joined to the distal end nodal ring by a joining portion obtained by radiating the laser light.

As a result, as shown in FIG. 6F, the distal end nodal ring 14 on which the laser light has been radiated and one end side end portion of the pulling wire 13 can be joined and fixed by a joining portion 16. That is, as shown in FIG. 3, the bending portion 6 in which the one end side of each pulling wire 13 is fixed to the inner circumferential face 14*i* of the distal end nodal ring 14 is obtained.

As described above, the distal end rigid member 20 is provided with the accommodating grooves 30 capable of accommodating end portions of the pulling wires 13, respectively; the one end side end portions of the pulling wires 13 are accommodated in the accommodating grooves 30; and, after that, the distal end nodal ring 14 is fitted to the small diameter portion 23 provided with the accommodating grooves 30. Consequently, one end portion of each pulling wire 13 can be sandwiched and held between the small diameter portion 23 and the distal end nodal ring 14.

In the held state, the accommodating grooves 30 of the distal end rigid member 20 and the first through holes 14*h* of the distal end nodal ring 14 are arranged on straight lines, respectively, along the longitudinal axis a2. Consequently, at the time of causing each pulling wire 13 to extend to the nodal ring proximal end side along the inner circumferential face 14*i*, it is possible to visually confirm the pulling wire 13 by causing the pulling wire 13 to pass immediately below a corresponding first through hole 14*h* and grasp that the one end portion side of the pulling wire 13 is accommodated at a predetermined position.

After that, the operator can grasp a position of the pulling wire 13 arranged on the inner circumferential face 14*i* side of the distal end nodal ring 14 from positions of a corresponding accommodating groove 30 and first through hole 14*h* to perform welding work. That is, the operator can grasp the arrangement position of the pulling wire 13 and efficiently and certainly perform welding work for welding the pulling wire 13 to the distal end nodal ring 14 with a high accuracy.

Moreover, since a jig for connecting the pulling wire 13 to the distal end nodal ring 14 becomes unnecessary, manufacturing costs can be further reduced.

Since the one end side of each pulling wire 13 can be directly joined to the inner circumferential face 14*i* of the distal end nodal ring 14 by welding, a connection member or a wire fixing portion that can cause an internal space on a central axis side of the insertion portion 2 in which the pulling wire 13 is inserted to be narrow become unnecessary, so that the diameter of the insertion portion 2 can be reduced.

By each accommodating groove 30 being configured with the wire accommodating portion 31 provided in the small diameter portion 23 and the relief portion 32 provided in the intermediate portion 22, it is possible to conveniently accommodate the one end side end portions of the pulling wires 13 into the accommodating grooves 30 without performing end portion processing of the pulling wire 13.

Note that each accommodating groove 30 may be configured only with the wire accommodating portion 31 provided in the small diameter portion 23. In this case, after newly performing end portion processing work for processing the end portion of each pulling wire 13, the processed one end side end portion of the pulling wire 13 is accommodated into the wire accommodating portion 31.

Figure 7:
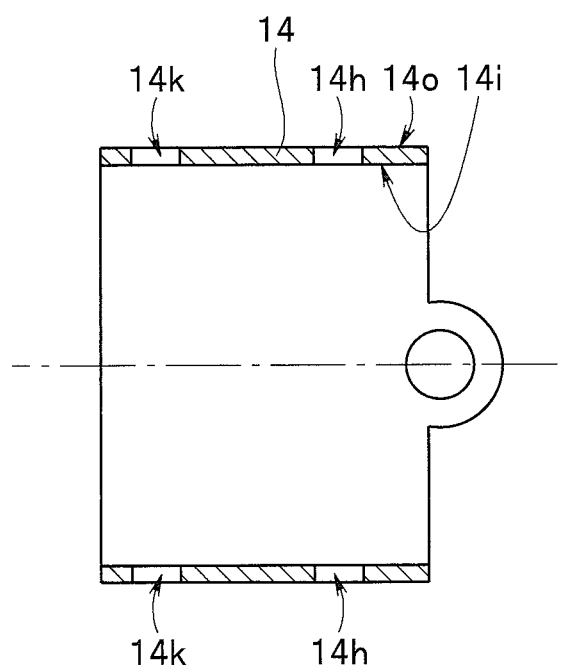
FIG. 7 is a diagram illustrating the distal end nodal ring provided with first through holes and second through holes.

In the embodiment described above, the first through holes 14*h* are formed in the distal end nodal ring 14. However, as shown in FIG. 7, second through holes 14*k* may be formed in the distal end nodal ring 14 on a distal end side or proximal end side of the first through holes 14*h*, respectively, in addition to the first through holes 14*h*. Then, the distal end nodal ring 14 including the first through holes 14*h* and the second through holes 14*k* is provided on the distal end rigid member 20.

Note that each second through hole 14*k* is used as both of a window for visually confirming whether a pulling wire 13 is arranged or not and an indicator to specify a range within which laser light is to be radiated at the time of welding the pulling wire 13 to the distal end nodal ring 14 similarly to each first through hole 14*h*. The first through holes 14*h* and the second through holes 14*k* provided on the distal end nodal ring 14 are provided being separated by a predetermined distance L along a nodal ring center, respectively. The distance L is a length required for welding fixation.

According to the configuration, by arranging the pulling wires 13 immediately below the first through holes 14*h* and the second through holes 14*k*, respectively, it is possible to more certainly grasp a position of the pulling wire 13 arranged on the inner circumferential face 14*i* side of the distal end nodal ring 14 and more easily and certainly grasp a welding range to perform welding work.

As a result, it is possible to firmly join and fix the one end side end portion of the pulling wire 13 to the distal end nodal ring 14 without measuring length dimensions of the joining portion 16.

Note that when the bending portion 6 is configured using the distal end nodal ring 14 shown in FIG. 7, the accommodating grooves 30 of the distal end rigid member 20 may be unnecessary. In this case, after arranging the end portion of each pulling wire 13 in a corresponding second through hole 14*k*, the pulling wire 13 is temporarily fixed to the distal end nodal ring 14 by welding. After that, the pulling wire 13 is caused to pass immediately below a corresponding first through hole 14*h*. While the state is being kept, welding between the first through hole 14*h* and the second through hole 14*k* is performed to provide the joining portion 16 described above, and the pulling wire 13 is fixed to the distal end nodal ring 14.

After that, the distal end nodal ring 14 to which the pulling wires 13 are joined is arranged on the small diameter portion 23 of the distal end rigid member 20 and fixed. Consequently, it is possible to provide the endoscope 1 provided with the bending portion 6 having operation and effects similar to the operation and effects of the embodiment described above.

According to the present invention, it is possible to, while reducing a diameter of an endoscope insertion portion, provide such an endoscope that pulling wires are efficiently welded with a high accuracy at predetermined positions of a tubular member constituting a bending portion, and cost reduction is realized.

The present invention is not limited to only the embodiment described above, but various modifications can be implemented within a range not departing from the spirit of the invention.

What is claimed is:

1. An endoscope comprising:
   a wire comprising a first end portion and a second end portion, the wire being inserted in an endoscope insertion portion;
   a tubular member, the first end portion of the wire being arranged along an inner circumferential face of the tubular member, the first end portion of the wire being joined at a predetermined position on a distal end of the tubular member by welding, the wire being arranged immediately below a first through hole including openings at predetermined positions on the inner circumferential face and an outer circumferential face of the tubular member;

a distal end member comprising:
  a small diameter portion fitted in a distal end side of the inner circumferential face of the tubular member,
  an intermediate diameter portion provided on a distal end side of the small diameter portion, the intermediate diameter portion having a diameter larger than a diameter of the small diameter portion, and
  a large diameter portion provided on a distal end side of the intermediate diameter portion, the large diameter portion having a diameter larger than a diameter of the intermediate diameter portion; and
an accommodating portion formed on an outer circumferential face of at least the small diameter portion, the first end portion of the wire being accommodated in the accommodating portion;
wherein the accommodating portion is a groove;
a depth of the accommodating portion from the outer circumferential face of the small diameter portion is same as an outer diameter dimension of the wire or smaller than the outer diameter dimension of the wire by a predetermined dimension;
the accommodating portion extends into the intermediate diameter portion to form a relief portion, the relief portion includes a terminal end in the intermediate diameter portion; and
the relief portion is formed such that a width and a depth of the relief portion in the intermediate diameter portion are the same as or larger than a width and the depth of the accommodating portion in the small diameter portion.

2. The endoscope according to claim 1, wherein the accommodating portion and the first through hole are provided on one straight line along a longitudinal axis of the endoscope insertion portion.

3. The endoscope according to claim 1, wherein the tubular member includes, in addition to the first through hole, a second through hole including openings on the inner circumferential face and the outer circumferential face, at a position separated from the first through hole by a predetermined distance along the longitudinal axis of the endoscope insertion portion.

4. The endoscope according to claim 1, wherein the tubular member is a distal end tubular member provided on a distal end of a bending portion provided in a middle of the endoscope insertion portion.

5. The endoscope according to claim 1, wherein a distal end face of the tubular member being positioned proximally relative to each of the intermediate diameter portion and the large diameter portion such that the first end portion of the wire is sandwiched between the distal end side of the inner circumferential face of the tubular member and a bottom surface of the accommodating portion and the wire is exposed through the first through hole.

6. The endoscope according to claim 1, wherein the distal end member is shorter in longitudinal length that the tubular member.

7. An endoscope comprising:
a wire comprising a first end portion and a second end portion, the wire being inserted in an endoscope insertion portion;
a tubular member, the first end portion of the wire being arranged along an inner circumferential face of the tubular member, the first end portion of the wire being joined at a predetermined position on a distal end of the tubular member by welding, the wire being arranged immediately below a first through hole including openings at predetermined positions on the inner circumferential face and an outer circumferential face of the tubular member;
a distal end member comprising:
  a small diameter portion fitted in a distal end side of the inner circumferential face of the tubular member,
  an intermediate diameter portion provided on a distal end side of the small diameter portion, the intermediate diameter portion having a diameter larger than a diameter of the small diameter portion, and
  a large diameter portion provided on a distal end side of the intermediate diameter portion, the large diameter portion having a diameter larger than a diameter of the intermediate diameter portion; and
an accommodating portion formed on an outer circumferential face of at least the small diameter portion, the first end portion of the wire being accommodated in the accommodating portion;
wherein the wire is welded to the tubular member between the first through hole and the accommodating portion;
a depth of the accommodating portion from the outer circumferential face of the small diameter portion is same as an outer diameter dimension of the wire or smaller than the outer diameter dimension of the wire by a predetermined dimension;
the accommodating portion extends into the intermediate diameter portion to form a relief portion, the relief portion includes a terminal end in the intermediate diameter portion; and
the relief portion is formed such that a width and a depth of the relief portion in the intermediate diameter portion are the same as or larger than a width and the depth of the accommodating portion in the small diameter portion.

* * * * *